United States Patent
Couto

(10) Patent No.: US 12,264,193 B2
(45) Date of Patent: Apr. 1, 2025

(54) METHOD FOR PRODUCING A RECOMBINANT ALLOTYPESPECIFIC RABBIT MONOCLONAL ANTIBODY

(71) Applicant: ABCAM LIMITED, Cambridge (GB)

(72) Inventor: Fernando Jose Rebelo Do Couto, Pleasanton, CA (US)

(73) Assignee: ABCAM LIMITED, Cambridge (GB)

( * ) Notice: Subject to any disclaimer, the term of this patent is extended or adjusted under 35 U.S.C. 154(b) by 1127 days.

(21) Appl. No.: 15/533,983

(22) PCT Filed: Dec. 10, 2015

(86) PCT No.: PCT/GB2015/053787
§ 371 (c)(1),
(2) Date: Jun. 7, 2017

(87) PCT Pub. No.: WO2016/092315
PCT Pub. Date: Jun. 16, 2016

(65) Prior Publication Data
US 2018/0009875 A1    Jan. 11, 2018

(30) Foreign Application Priority Data
Dec. 11, 2014   (GB) ..................... 1422075

(51) Int. Cl.
| C12N 15/11 | (2006.01) |
| C07K 16/00 | (2006.01) |
| C12N 5/20  | (2006.01) |
| C12N 15/10 | (2006.01) |

(52) U.S. Cl.
CPC .......... *C07K 16/00* (2013.01); *C07K 2317/10* (2013.01); *C07K 2317/20* (2013.01); *C07K 2317/51* (2013.01); *C07K 2317/515* (2013.01)

(58) Field of Classification Search
None
See application file for complete search history.

(56) References Cited

U.S. PATENT DOCUMENTS

| 7,429,487 B2* | 9/2008 | Pytela .................... C12P 21/005 |
|  |  | 435/328 |
| 2003/0104410 A1 | 6/2003 | Mittmann |
| 2004/0067496 A1* | 4/2004 | Pytela ................. C07K 16/2839 |
|  |  | 435/6.14 |
| 2016/0053009 A1* | 2/2016 | Peterson ................ C07K 16/26 |
|  |  | 435/6.12 |

FOREIGN PATENT DOCUMENTS

| CA | 2767231 A1 | 1/2011 |
| CN | 101255194 A1 | 9/2008 |
| WO | WO 2009/111729 | 9/2009 |
| WO | WO 2009/113742 | 9/2009 |

OTHER PUBLICATIONS

Popkov et al, Rabbit Immune Repertoires as Sources for Therapeutic Monoclonal Antibodies: The Impact of Kappa Allotype-correlated Variation in Cysteine Content on Antibody Libraries Selected by, J. Mol. Biol. (2003) pp. 325-335.*
Wolf and Liu, Identification of rabbit immunoglobulin latent Ck1 allotype genes alters the concept of allelic inheritance, Molecular Immunology, 1998, pp. 965-976.*
Buck et al, Design Strategies and Performance of CUstom DNA Sequencing Primers, BioTecnhiques, 1999, pp. 528-536.*
Cochet et al, Selective PCR Amplification of Functional Immunoglobulin Light Chain from Hybridoma Containing the Aberrant MOPC 21-Derived Vk by PNA-Mediated PCR Clamping , Biotechiques, 1999, pp. 818-822.*
Akimenko et al., "Complex allotypes of the rabbit immunoglobulin Kappa Light Chains are Encoded by Structural Alleles", Nucleic Acids Research, Information Retrieval Ltd., 1984, 12(11): 4691-4701.
Dreher et al., "cDNA clone encoding a complete rabbit immunoglobulin Kappa light chain of b4 allotype", Proceedings of the National Academy of Sciences, 1983, 80:4489-4493.
Seeber et al., "A Robust High Throughput Platform to Generate Functional Recombinant Monoclonal Antibodies Using Rabbit B Cells from Peripheral Blood", PLoS One, 2014, 9(2):e86184.
Spieker-Polet et al., "Rabbit monoclonal antibodies: Generating a fusion partner to produce rabbit-rabbit hybridomas", Proceedings of the National Academy of Sciences, 1995, 92: 9348-9352.
Van Der Loo et al., "The allotypic patchwork pattern of the rabbit IGKC1 allele b5wf: genic exchange or common ancestry?" Immunogenetics, 1999, 49(1):7-14.
Wolf et al., "Identification of rabbit immunoglobulin latent Ckappa1 allotype genes alters the concept of allelic inheritance", Molecular Immunology, 1998, 35: 965-976.
Database Registry [Online], Chemical Abstracts Service, 2005, XP-002755298, Database accession No. 843725-58-6.

(Continued)

*Primary Examiner* — Maria Marvich
(74) *Attorney, Agent, or Firm* — James S. Keddie; Bozicevic, Field & Francis LLP

(57) ABSTRACT

A method for cloning a full length coding sequence for a light chain of a rabbit monoclonal antibody is provided. In some embodiments, this method may involve: fusing a B cell from a rabbit having a B4 allotype with a 240E cell or a derivative thereof to produce a hybridoma, wherein the B cell and the hybridoma produce a monoclonal antibody; making cDNA from the hybridoma; amplifying from the cDNA a full length coding sequence for the light chain of a monoclonal antibody produced by the hybridoma using: a forward primer that hybridizes to a site in SEQ ID NO: 10, and a reverse primer having a 3' end of sequence CTARCAGTCX (SEQ ID NO: 11), wherein R is A or G and X is A, AC, ACC or ACCC; and cloning the amplified sequence into an expression vector to produce a first plasmid.

11 Claims, 3 Drawing Sheets
Specification includes a Sequence Listing.

(56) References Cited

OTHER PUBLICATIONS

Database Registry [Online], Chemical Abstracts Service, 2004, XP-002755299, Database accession No. 795419-85-1.
Database Registry [Online], Chemical Abstracts Service, 2004, XP-002755300, Database accession No. 722438-22-4.
Abcam website, available online at http://www.abcam.com/primary-antibodies/rabmab-technology-the-need-the-attempts-and-the-breakthrough, accessed Sep. 9, 2015.
Akcesme, "Efficient Algorithm for Primer Design", Southeast Europe Journal of Soft Computing, 2013, 2(2): 78-82.
Biocompare, "Primers, by Design—Tips for Optimal DNA Primer Design", Authored in 2013 and downloaded from the Biocompare website on Sep. 7, 2021, http://www.biocompare.com/Bench-Tips/133581-Primers-by-Design-Tips-for-Optimal-DNA-Primer-Design/.
Dieffenback et al., "PCR Methods Appl. General concepts for PCR Primer Design", Cold Spring Harbor Laboratory Press, 1993, 3: S30-S37.
Lorenz, "Polymerase Chain Reaction: Basic Protocol Plus Troubleshooting and Optimization Strategies", Journal of Visualized Experiments, 2012, 63: e3998, 15 pages.
Thornton et al., "Real-Time PCR (qPCR) Primer Design Using Free Online Software", 2011, Biochemistry and Molecular Biology Education, 2011, 39(2): 145-154.

\* cited by examiner

```
                                    ATGGACACGAGGGCCCCCAC-3'
CAGTGCAGGCAGGACCCAGCATGGACACGAGGGCCCCCACTCAGCTGCTGGGGCTCCTGCTGCTCTGG
                       M   D   T   R   A   P   T   Q   L   L   G   L   L   L   W
```

FIG. 1

```
       G   T   T   S   V   V   Q   S   F   N   R   G   D   C   *
      GGCACGACCTCAGTCGTCCAGAGCTTCAATAGGGGTGACTGTTAGAGCGAGACGCCTG
                                        ||||||||||
                                    3'-XCTGACAATC
```

FIG. 2

METHOD FOR PRODUCING A RECOMBINANT ALLOTYPESPECIFIC RABBIT MONOCLONAL ANTIBODY

The invention relates to a method of producing a rabbit monoclonal antibody in an allotype-specific manner by selectively amplifying antibodies having a b4 allotype. The invention further relates to use of the primers and compositions thereof.

BACKGROUND

Rabbit monoclonal antibodies are valued both as diagnostic and research reagents, due to the inherent ability of the rabbit antibody repertoire to recognise different epitopes to those seen by mouse antibodies (1-3) and in addition, rabbit antibodies often exhibit higher binding affinity making them suitable candidates for therapeutic development.

The development of rabbit myeloma cell lines (rabbit fusion partners) has allowed the efficient generation of rabbit hybridomas for the production of monoclonal antibodies to a range of targets (4-6). However, many such hybridomas actually produce two antibodies, one from the fusion partner (the "endogenous" antibody) and the other from the fused B cell (the "monoclonal" antibody). In many cases the amount of endogenous antibody far exceeds the amount of monoclonal antibody, which can make it difficult, if not impossible, to clone sequences encoding the desired monoclonal antibody efficiently. U.S. Pat. No. 7,429,487 describes one method where rabbit-derived immortal B-lymphocytes lacking an endogenous heavy chain are fused with B-lymphocytes to produce hybridomas that express antibodies having a heavy chain derived from the antibody-producing spleen B cell (and not the immortal cell).

The rabbit antibody is somewhat simplified compared with mouse and human and rabbit IgG has no subclass and consists of two heavy and two light chains. The rabbit heavy chain is represented by the $V_Ha+$ allotype in 70 to 90% of B-cells. The three alleles of $V_H1$ in laboratory strains, $V_H1a1$, $V_H1a2$ and $V_H1a3$, encode allotypes a1, a2 and a3, respectively. The other 10 to 30 percent of IgG in serum and mucosa are called VHa-negative ($V_Ha^-$) because they do not react with any anti-$V_Ha$ allotype antisera. The majority (90% to 95%) of the rabbit light chains is derived from Cκ1 (isotype κ1). Five allelic Cκ1 genes are known as OK allotypes b4, b4v, b5, b6 and b9. The Cκ2 gene encoding the isotype κ2 is rarely expressed, except in some b9 rabbits. Only 5 to 10 percent of total IgG light chains are isotype A.

The general complexities of rabbit immunoglobulin genes, somatic rearrangements, hypermutation and other sequence variations, means that rabbit individual light chain kappa sequences can vary significantly even if they are of a given allotype. This variation, in combination with the fact that the sequences of the different allotypes are quite similar to one another, can make it challenging to consistently amplify sequences of one kappa chain allotype at the expense of another, especially when the sequence of the target antibody that one wishes to amplify is not known.

Accordingly there is an ongoing need to develop new methods that improve the quality of the antibodies produced from rabbit hybridomas and to avoid the production of antibodies derived from the rabbit fusion partner. It is an object of the invention to provide alternative approaches to the methods described in U.S. Pat. No. 7,429,487.

The current invention provides a method to preferentially amplify and isolate antibodies of a b4 allotype at the expense of antibodies deriving from the fusion partner having a b5 allotype.

SUMMARY OF THE INVENTION

The applicants have found that allotypes b4 and b5 of the rabbit kappa light chain can be consistently discriminated using a four base motif nucleic acid primer that is proximal to the stop codon in those genes.

This motif and its proximity to the stop codon has allowed a discriminatory reverse primer to be designed that, when used in conjunction with a suitable forward primer, can consistently amplify b4 kappa light chain sequences that are full length, even in a sample that contains b5 kappa light chain sequences. The primer may be used, for example, in a method of producing a recombinant antibody where, in such a method, B cells from a rabbit that is homozygous for a b4 allotype are fused with rabbit myeloma cells or a derivative thereof which have an allotype other than b4, for example b5 (such as 240E cells), to produce a hybridoma expressing a full length sequence encoding the kappa light chain of the monoclonal antibody which can be selectively amplified. The amplified sequences can be cloned into an expression vector to facilitate expression of a recombinant antibody, which can then be purified.

According to a first aspect of the invention there is provided a method for producing a recombinant antibody, the method comprising the steps of:
  a) providing a rabbit antibody-producing B-lymphocyte having a b4 allotype;
  b) fusing the B-lymphocyte of step a) with a rabbit fusion partner or derivative thereof having an allotype other than b4 to produce a hybridoma cell capable of producing an antibody;
  c) isolating cDNA from the hybridoma;
  d) amplifying the heavy chain variable domain and the light chain from the cDNA of step c) using:
    (i) a light chain primer pair that comprises a forward primer having a 3' end of sequence according to SEQ ID No: 1 and a reverse primer having a 3' end of sequence according to SEQ ID No: 2, and (ii) a heavy chain primer pair that comprises a forward primer having a 3' end of sequence according to SEQ ID No: 3 and a reverse primer having a 3' end of sequence according to SEQ ID No: 4;
  e) cloning the amplified heavy chain domain and light chain obtained in step d) into one or more plasmids;
  f) transfecting the plasmids into a mammalian host cell capable of expressing an antibody;
  g) culturing the mammalian host cells under conditions suitable for antibody production;
  h) isolating the antibodies produced in step g).

According to a further aspect there is provided an isolated (synthetic, recombinant) nucleic acid molecule according to SEQ ID No: 11

According to a further aspect of the invention there is provided use of an isolated synthetic nucleic acid molecule having a 3' end of sequence according to SEQ ID No: 11 in the production of a recombinant antibody derived from a rabbit having a b4 allotype.

According to a further aspect of the invention there is provided a composition for amplifying a heavy and light chain antibody domain derived from a rabbit having a b4 allotype, the composition comprising a primer pair wherein one of the primers has a 3' end of sequence according to SEQ ID No: 11.

BRIEF DESCRIPTION OF THE FIGURES

The skilled artisan will understand that the drawings, described below, are for illustration purposes only. The drawings are not intended to limit the scope of the present teachings in any way.

FIG. 1 shows an alignment of the 5' end of an exemplary b4 kappa light chain cDNA sequence (SEQ ID No: 10) and a forward primer having a 3' end of sequence ATGGACACGAGGGCCCCCAC (SEQ ID No: 1). The encoded amino acid sequence is SEQ ID No: 13.

FIG. 2 shows an alignment of the 3' end an exemplary b4 kappa light chain cDNA sequence (SEQ ID No: 14) and a reverse primer having a 3' end of sequence CTAACAGTCX (SEQ ID NO: 2) where X is A, AC, ACC or ACCC. The encoded amino acid sequence is SEQ ID No: 15.

DETAILED DESCRIPTION

Figure 3:
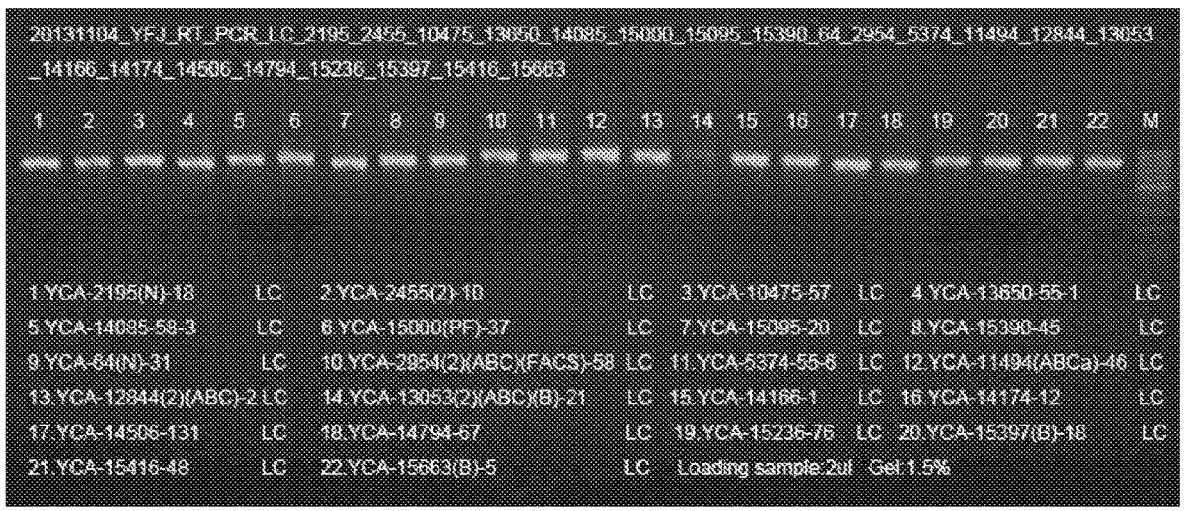
FIG. 3 shows agarose gel electrophoresis of full length light chain amplicons obtained from using the present method (a forward primer of sequence (SEQ ID NO: 6) and a reverse primer of sequence (SEQ ID NO: 7) on 44 different hybridomas FIG. 4 shows a panel of hybridoma cell lines derived from the 240E-W fusion partner expressing variable amounts of an endogenous Ig heavy chain. Hybridoma lines derived from 240E-W secrete endogenous Ig heavy and light chains. IgG proteins secreted by six different rabbit hybridoma lines were analyzed by western blotting with goat-anti rabbit IgG antibodies. The protein bands at approx. 50 kDa correspond to Ig heavy chains, the bands at approx. 25 kDa to Ig kappa light chains. Each clone produces a spleen-derived light chain (spleno-L chain) of slightly variable size (lower band), and a 240E-W-derived light chain (endo-L chain) of constant size (upper band).
Figure 3:
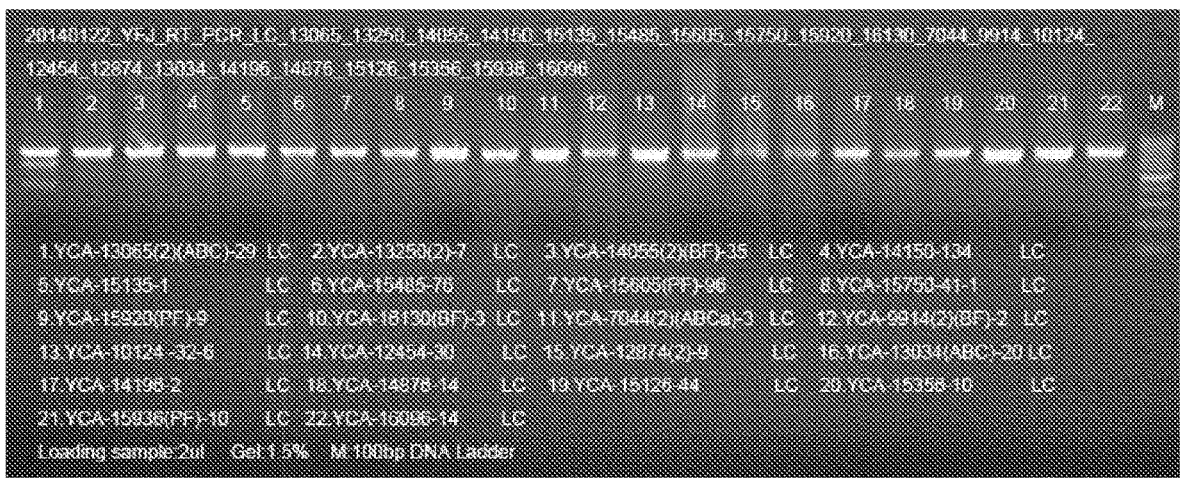
Figure 4:
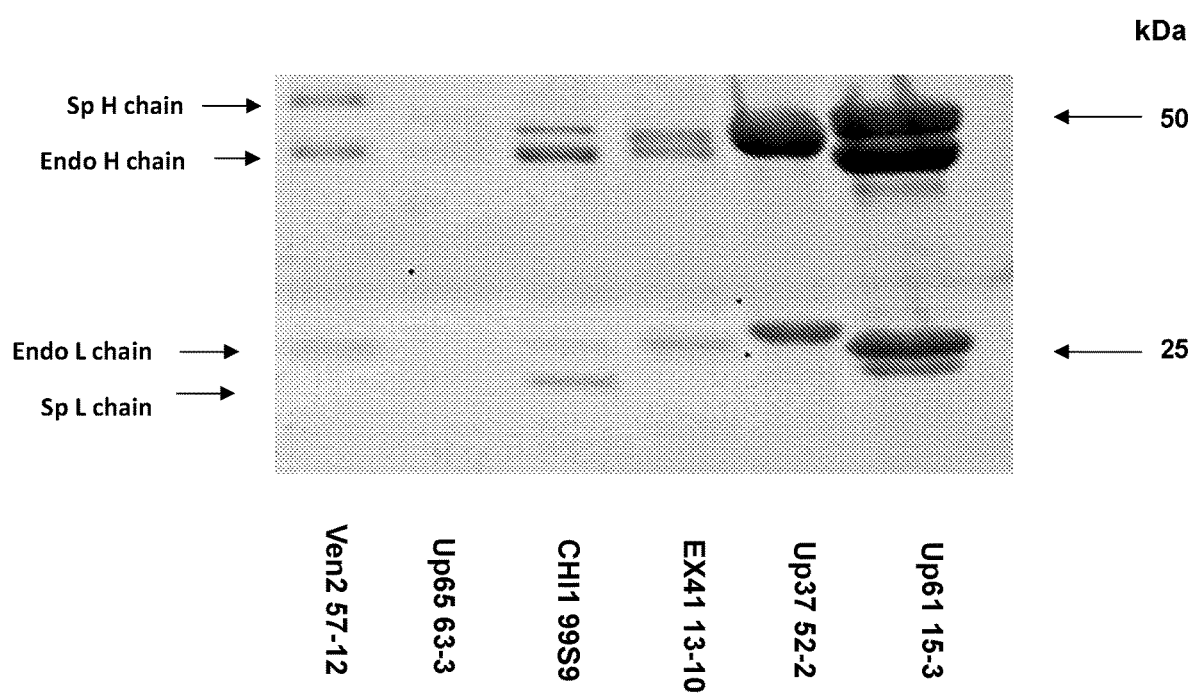

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

According to a first aspect of the invention there is provided a method for producing a recombinant antibody, the method comprising the steps of:
a) providing a rabbit antibody-producing B-lymphocyte having a b4 allotype;
b) fusing the B-lymphocyte of step a) with a rabbit fusion partner or derivative thereof having an allotype other than b4 to produce a hybridoma cell capable of producing an antibody;
c) isolating cDNA from the hybridoma;
d) amplifying the heavy chain variable domain and the light chain from the cDNA of step c) using:
   (i) a light chain primer pair that comprises a forward primer having a 3' end of sequence according to SEQ ID No: 1 and a reverse primer having a 3' end of sequence according to SEQ ID No: 2; and (ii) a heavy chain primer pair that comprises a forward primer having a 3' end of sequence according to SEQ ID No: 3 and a reverse primer having a 3' end of sequence according to SEQ ID NO: 4;
e) cloning the amplified heavy chain domain and light chain obtained in step d) into one or more plasmids;
f) transfecting the plasmids into a mammalian host cell capable of expressing an antibody;
g) culturing the mammalian host cells under conditions suitable for antibody production;
h) isolating the antibodies produced in step g).

The method further comprises the optional step of i) purifying the antibodies obtained in step h).

The rabbit fusion partner used in the method may be a 240E cell or derivative thereof having a b5 allotype. The light chain forward primer, the light chain reverse primer, the heavy chain forward primer and the heavy chain reverse primer may further comprise a restriction site. The method may use a light chain forward primer has a 3' end of sequence according to SEQ ID No: 6, the light chain reverse primer has a 3' end of sequence according to SEQ ID No: 7, the heavy chain forward primer has a 3' end of sequence according to SEQ ID No: 8 and the heavy chain reverse primer has a 3' end of sequence according to SEQ ID No: 9. The heavy and light chains may be amplified in the same reaction by multiplex PCR.

The heavy and light chains may be cloned into separate plasmids.

The method described herein is based on novel primers that have been designed to allow b4 allotype antibodies to be preferentially expressed in favour of b5 allotype antibodies, further to the generation of a hybridoma. This provides a new method for selectively producing the desired antibody in a direct and efficient manner, thereby avoiding additional selection and purification steps. A further advantage of the method is the reduction of contamination with "endogenous b5" which can lead to dysfunction of IgG.

The method provides for the production of a full length antibody. Reference herein to "full length" refers to a sequence that contains both the start and stop codons of a DNA sequence encoding a polypeptide. For example, it will be appreciated that a "full length light chain" comprises both the variable light chain domain and the light chain constant region.

In view of the limited number of rabbit hybridomas successfully generated for the production of antibodies and the difficulties associated with their production (Weimin Zhu, Guo-Liang Yu, "Rabbit Hybridoma" Book Chapter p 151-168. "Therapeutic Monoclonal Antibodies: from bench to clinic", A John Wiley & Sons, Inc., Publication 2009) the current invention is particularly useful when employed with 240E cell lines and derivatives thereof which all are characterised in having a b5 allotype.

It will be appreciated that the invention may be employed for use with rabbit fusion partners having a b5 allotype. The invention may also be used with rabbit fusion partners having a b6 or b95 allotype provided that the primers are capable of differentiating between the b4 allotype and the allotype of the fusion partner.

In one embodiment, a rabbit fusion partner or derivative thereof having an allotype other than b4 is selected from a 240E cell or derivative thereof.

Reference herein to "allotype" in the context of antibodies refers to inherited allelic variants arising from genetic differences between individuals which may be recognised as antigenic by members of the same species.

For the purposes of this invention and in the context of fusion with a rabbit immortal cell reference herein to "B-lymphocytes" or "B-cells" refers to cells responsible for mediating the adaptive immune response which are capable of producing an antibody in response to antigen binding and activation. Sources of antibody-producing B lymphocytes include spleen, bone marrow, lymph node or other lymph organs and circulatory white blood cells.

Rabbit antibody-producing B-lymphocytes, having a b4 allotype for example, may be isolated and obtained using conventional methods known in the art following immunisation of a rabbit with an antigen and establishment of a suitable immune response. Typically rabbit antibody-producing B-lymphocytes are isolated from the spleen of an immunised rabbit. Procedures for immunisation are known in the art and are described in Harlow (Antibodies: A Laboratory Manual, First Edition (1988) Cold Spring Harbour, N.Y.) and Weir (Handbook of Experimental Immunology Vol 4, Blackwell Scientific Publishers, Oxford, England, 1986).

References herein to "antibody" or "immunoglobulin" which are used interchangeably refer to tetrameric molecules made up of paired heterodimers (each comprising one heavy and one light chain) stabilised and cross-linked by inter-chain and intra-chain disulphide bonds that specifically bind to antigen. The light chains may be of either the kappa or lambda isotype.

Antibodies as described herein may include antibodies of any isotype, fragments of antibodies which retain specific binding to antigen, including, but are not limited to, Fab, Fv, scFv, VH and VL domains, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of the biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bifunctional (i.e., bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed., 1984, and Hunkapiller and Hood, Nature, 323, 15-16 (1986)).

An immunoglobulin light or heavy chain variable region or domain (VH or VL) consists of a framework region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The isolation of 240E cells, also referred herein to rabbit fusion partners, myelomas or plasmacytoma and methods of production have been described in the literature (U.S. Pat. No. 5,675,063; Spieker-Polet (Proc. Natl. Acad. Sci. 1995 92:9348-52). It will be understood that such cell lines are immortalized and are characterised by the presence of one or more oncogenes such as v-abl and c-myc, for example. For the avoidance of doubt, reference to "240E" and derivatives thereof includes all derivatives of 240E that are characterised as having a b5 allotype. For example cell lines 240E-1, 240E1-1-2 (as described in U.S. Pat. No. 5,675,063 and Spieker-Polet et al, Proc. Natl. Acad. Sci. 1995 92:9348-52, incorporated herein by reference), and deposited at the ATCC as accession no. HB-11870). 240E-W and 240E-W2 are also included within the scope of the invention (Weimin Zhu, Guo-Liang Yu, "Rabbit Hybridoma" Book Chapter p 151-168. "Therapeutic Monoclonal Antibodies: from bench to clinic", A John Wiley & Sons, Inc., Publication 2009).

The term "derivative thereof" as used herein, refers to a cell that is derived from 240E through successive rounds of plating and selection, e.g., to increase the fusion rate, decrease or abolish expression of the endogenous antibody, to increase stability, to increase antibody expression, etc. A derivative of 240E will have the same basic characteristics of 240E (i.e., immortality and an ability to fuse with a B cell to produce a hybridoma that produces the antibody encoded by the B cell) but some of the characteristics (e.g., fusion rate, expression level of the endogenous antibody, stability, etc.) may be different. Derivatives of 240E are described in U.S. Pat. No. 7,429,487.

Methods for fusing an antibody-producing B-cell with a rabbit fusion partner are known in the art and described in the literature (Yam et al, Methods Mol. Biol. 2014, 1131: 71-9; Spieker-Polet et al, Proc. Natl. Acad. Sci. 1995, 92:9348-52; U.S. Pat. Nos. 5,675,063and 7,429,487). The term "hybridoma" refers to the cell produced as a result of fusion between a B cell and a fusion partner. Such a hybridoma does not need to be stable.

With reference to a hybridoma, the term "endogenous antibody" as used herein, refers to the antibody that is encoded by genetic material donated to the hybrid by the fusion partner. The fusion partner produces the endogenous antibody prior to fusion, and the hybridoma is able to still make that antibody.

With reference to a hybridoma, the term "monoclonal" as used herein, refers to the antibody that is encoded by genetic material donated to the hybrid by the B cell.

The method comprises the step of isolating c-DNA from the hybridoma produced and may be performed using standard procedures, for example, firstly extracting mRNA from the lysates of the hybridomas and then carrying out a cDNA synthesis reaction, as described in the methods herein, to produce a DNA fragment that serves as a template for amplification of the antibody heavy and light chain domains, or full length heavy and light chains.

In one example the 5' end of an exemplary b4 kappa light chain cDNA sequence is according to SEQ ID No: 10 and shown in FIG. 1. SEQ ID No: 10 shows the start codon (ATG) underlined for the light chain coding sequence domain.

In one example the 3' end of an exemplary b4 kappa light chain cDNA sequence is according to SEQ ID No: 14 as shown in FIG. 2. The stop codon TAG is underlined.

Sequences encoding the antibody heavy and light chains are amplified from the cDNA using techniques well known in the art, such as Polymerase Chain Reaction (PCR), U.S. Pat. Nos. 4,683,195 and 4,683,195; Polymerase chain Reaction: Current Communication in Molecular Biology, Cold Springs Harbour Press, Cold Spring Harbour, N.Y., 1989. Oligonucleotide primer pairs spanning the start and stop codons of the heavy and light chain cDNAs are able to amplify the full length heavy and light chain polynucleotides, or the VH and VL domains.

The term "primer" as used herein, is well known in the art and refers to an oligonucleotide that has a 3' hydroxyl that is capable, upon forming a duplex with a polynucleotide template, of acting as a point of initiation of nucleic acid synthesis and being extended from its 3' end along the template to form an extended duplex. The sequence of nucleotides added during the extension process is determined by the sequence of the template polynucleotide. Primers are generally of a length compatible with their use and are usually in the range of between 8 to 100 nucleotides in length, e.g., 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges.

The term "primer pair" used herein is known in the art and refers to a forward primer and a reverse primer, where the forward primer and reverse primer prime towards one another and, when employed in polymerase chain reaction (PCR) with a suitable template, amplify a double-stranded DNA fragment or amplicon. Reference to a primer as being a "forward" or "reverse" primer herein is arbitrary, unless specifically indicated otherwise. It will be appreciated that the term "3' end of sequence" as used herein, refers to a sequence that is at the 3' terminus of a primer. For example, a primer having a 3' end of sequence CTARCAGTCX (SEQ ID No: 11) written out formally is CTARCAGTCX-3', where the nucleotide defined by X has a hydroxyl and is extendible by a polymerase.

Certain primers described herein may be described using a formula. A primer described by the formula may be encompassed by the formula or a may be mixture of primers that are encompassed by the formula. For example, a primer that has a 3' end defined by the formula: "CTARCAGTCX (SEQ ID No:11), wherein R is A or G and X is A, AC, ACC or ACCC", may be represented by a single primer that has a 3' end sequence of CTAACAGTCACA (SEQ ID No:16), CTAGCAGTCACA (SEQ ID No:17), CTAACAGTCACC (SEQ ID No:18), CTAGCAGTCACC (SEQ ID No:19), CTAACAGTCACC (SEQ ID No:5), CTAGCAGTCACC (SEQ ID No:20), CTAACAGTCACCC (SEQ ID No:21) or CTAGCAGTCACCC (SEQ ID No:22), or a mixture of any number of the same. As would be understood, any number of nucleotides (e.g., up to 10, up to 20, up to 30 or up to 40 nucleotides) may be present at the 5' end of a primer that has a defined 3' end. A primer may have a 3' end that has at least 10, at least 15 or at least 20 nucleotides of complementarity with its target.

In one embodiment the forward kappa light chain b4 primer (forward primer) has a 3' end sequence ATGGACACGAGGGCCCCCAC (SEQ ID No: 1) as shown in FIG. 1. It will be appreciated that the sequence of the forward primer may vary considerably according to the nucleotide sequence of the 5' end of the light chain DNA fragment to be amplified. The forward primer may be designed to hybridize upstream or downstream of the ATG sequence. The forward primer may further comprise a restriction site, for example KpnI, which facilitates enzyme cleavage and cloning of the 5' end of the coding sequence.

In another example the forward primer has a 3' end sequence CGCAAGCTTGTACCCTTCACC<u>ATG</u>GACACGAGGGCCCCCAC (SEQ ID No: 6), which comprises a KpnI restriction site (CCATGG) that includes the ATG.

The primers according to SEQ ID No: 1 and SEQ ID No: 6 hybridise to the kappa light chain cDNA sequence at the 5' end of the full length light chain coding sequence. Therefore the full length kappa light chain (i.e. VL domain plus constant region) is amplified when used with any of the light chain reverse primers described herein.

In one embodiment the reverse kappa light chain b4 primer has a 3' end of sequence of formula CTARCAGTCX (SEQ ID No. 11) where R is A or G and X may be selected from A, AC, ACC and ACCC. In one example the reverse primer is represented by <u>CTA</u>ACAGTCX (SEQ ID No: 2) and the underlined sequence corresponds to the stop codon as shown in FIG. 2.

In a further embodiment the 3' end of the reverse primer may be of sequence CTARCAGTCACC (SEQ ID No: 12), where R is A or G, or CTAACAGTCACC (SEQ ID No: 5). Further examples of the 3' end of reverse kappa light chain b4 primers according to SEQ ID No. 11 may be selected from SEQ ID No: 16, SEQ ID No: 17, SEQ ID No: 18, SEQ ID No: 19, SEQ ID No: 20, SEQ ID No: 21 and SEQ ID No: 22.

As shown in FIG. 2, the 3' end of the reverse primer base pairs with three or four bases of the b4-specific GGTG motif (underlined) as well as, optionally, one more base that is 3' to the b4-specific motif. The applicants identified the specific GGTG motif as being unique to the b4 allotype compared for example with the AAGA motif found in b5 allotypes.

In a further embodiment the reverse primer may contain a site for a restriction enzyme (e.g., NotI) which is 5' to the nucleotides corresponding to the stop codon in order to facilitate cloning of the 3' end of the coding sequence. In one example the reverse primer used may be of sequence (SEQ ID No: 7)
CGC<u>GCGGCCGC</u>TCTCRCT<u>CTA</u>ACAGTCACC, wherein R is A or G, and the underlined sequences correspond to the stop codon and a NotI restriction site.

In one embodiment, a full length kappa light chain domain sequence may be amplified using a forward primer having a 3' end of sequence according to SEQ ID No: 1 or SEQ ID No: 6 and a reverse primer having a 3' end of sequence according to SEQ ID No: 11.

In one embodiment the heavy chain forward and reverse primers may be designed so that they hybridise to sites that are proximal to the start and stop codons of a b4 rabbit allotype. It will be appreciated that suitable rabbit heavy chain primers to amplify heavy chain cDNA or variable region (VH) cDNA may be prepared by reference to conventional methods and that this is within the remit of the person skilled in the art.

In one example a forward heavy chain primer has a 3' end sequence <u>ATG</u>GAGACTGGGCTGCGCTGGCT (SEQ ID No: 3; ATG underlined). In another example a reverse heavy chain primer has a 3' end sequence CAGGCAGCCCAGGGGTCAC (SEQ ID No: 4).

The sequence of a b4 rabbit variable heavy chain domain (VH) may be amplified using a forward primer having a 3' end of sequence according to SEQ ID No: 3 or SEQ ID No: 8 and a reverse primer having a 3' end of sequence according to SEQ ID No: 4 or SEQ ID No: 9.

A b4 variable heavy chain domain and a b4 light chain may be amplified using a b4 light chain forward primer having a 3' end of sequence according to SEQ ID No: 1 or SEQ ID No: 6, a b4 light chain reverse primer having a 3' end of sequence according to SEQ ID No: 11 or SEQ ID No: 7, a b4 heavy chain forward primer having a 3' end of sequence according to SEQ ID No: 3 or SEQ ID No: 8 and a b4 heavy chain reverse primer having a 3' end of sequence according to SEQ ID No: 4 or SEQ ID No: 9 respectively.

The heavy and light chains may be amplified in the same reaction by multiplex PCR.

The heavy and light chain sequences may be cloned into separate plasmids, or the same plasmid. In some embodiments, the method may comprise amplifying a heavy chain coding sequence for the monoclonal antibody from the cDNA; and cloning the heavy chain coding sequence into a second expression vector to produce a second plasmid.

The amplified heavy and light chain amplicons can then be cloned into one or more plasmids. The plasmids can be introduced into a mammalian host cell (e.g., a bacterial, insect, plant, yeast or mammalian host cell such as HEK-293 cells, Vero cells, CHO cells, 3T3 cells, COS cells, etc.) and the cell incubated under conditions sufficient to induce expression of the encoded antibody. Vector systems and hosts for expressing antibodies are well known (see, e.g., Verma et al, J. Immunol. Methods. 1998216:165-81, Chartrain et al, Curr. Pharm. Biotechnol. 2008 9:447-67; Arbabi-Ghahroudi et al, Cancer Metastasis Rev. 2005 24:501-19 and Morrow (Biotechnol. Annu. Rev. 2007 13:95-113). In particular embodiments, a pTT5 vector (see, e.g., Jager et al, BMC Biotechnology 2013, 13:52 and You et al, Bioscience, Biotechnology, and Biochemistry 2013 77:1207-1213), may used, although other vector systems are available. As would be understood, the expression vector may comprise a promoter and terminator for expression of the heavy and light chains of a monoclonal antibody in a cell.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In most embodiments, the antibody is typically secreted into the supernatant of the media in which the cell is growing.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be preferred. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

In one embodiment, the invention relates to a method of cloning a full length coding sequence of a light chain rabbit monoclonal antibody, the method comprising the steps of:
  a) providing a rabbit antibody-producing B-lymphocyte having a b4 allotype;
  b) fusing the B-lymphocyte of step a) with a rabbit fusion partner or derivative thereof having an allotype other than b4 to produce a hybridoma cell capable of producing an antibody;
  c) isolating cDNA from the hybridoma;
  d) amplifying the light chain domain from the cDNA of step c) using:
    (i) a light chain primer pair that comprises (i) a forward primer having a 3' end of sequence that hybridizes to a site in SEQ ID No. 10 and (ii) a reverse primer having a 3' end of sequence according to SEQ ID No:11;
  e) cloning the amplified light chain domain obtained in step d) into a plasmid for expression.

The method may further comprise the additional step of
  f) expressing the light chain in a host cell.

The light chain domain may be isolated and purified from the host cells expressing them by techniques known in the art. Purification of light chain domains as referred to herein may be carried out by suitable methods known in the art. For example the light chain domains may be purified from the host cell or cell culture medium by chromatography, ion-exchange chromatography, size exclusion chromatography, high performance liquid chromatography (HPLC) and affinity chromatography (Methods in Enzymology, Vol. 182, Guide to Protein Purification, Eds. J. Abelson, M. Simon, Academic Press, 1st edition, 1990).

According to a further aspect of the invention there is provided a variety of compositions that are consistent with the methods described above.

In an embodiment there is provided a composition comprising;
  a) a cDNA sequence from a hybridoma produced by fusing an antibody-producing B cell from an rabbit having a B5 allotype and a 240E cell or a derivative thereof; and b) a PCR reagent comprising (i) a light chain primer pair that comprises a forward primer having a 3' end of sequence according to SEQ ID No: 1) and a reverse primer having a 3' end of sequence according to SEQ ID No:2; and (ii) a heavy chain primer pair that comprises a forward primer having a 3' end of sequence according to SEQ ID No: 3 and a reverse primer having a 3' end of sequence according to SEQ ID No: 4. The light chain reverse primer may have a 3' end of sequence according to SEQ ID NO: 5. The composition may comprise (i) the light chain primer pair comprising a forward primer having a 3' end of sequence according to SEQ ID No: 6 and a reverse primer having a 3' end of sequence according to SEQ ID No: 7, and (ii) the heavy chain primer pair comprises a forward primer having a 3' end of sequence according to SEQ ID No: 8 and a reverse primer having a 3' end of sequence according to SEQ ID No: 9.

The primer sequences according to the invention are listed in Table 1.

In one embodiment of the invention there is provided an isolated synthetic nucleic acid primer having a 3' end of sequence according to SEQ ID No: 11.

In one embodiment of the invention there is provided an isolated synthetic nucleic acid primer having a 3' end of sequence according to SEQ ID No: 2.

For the avoidance of doubt the term "synthetic" in the context of the invention, refers to a non-natural DNA sequence not found in nature.

In one embodiment there is provided an isolated synthetic nucleic acid molecule having a 3' end of sequence according to the formula represented by CTARCAGTCX (SEQ ID No. 11) where R may be A or G and X may be selected from A, AC, ACC and ACCC. In one example R is A and X is selected from A, AC, ACC and ACCC (e.g. SEQ ID No: 2). In another example R is G and X is selected from A, AC, ACC and ACCC.

In a further example X is ACC or ACCC and R is A or G (SEQ ID No. 12).

Specific examples of isolated synthetic nucleic acid molecules according to CTARCAGTCX (SEQ ID No. 11) which represent the 3' end sequence of a b4 kappa light chain reverse primer are listed below:

CTAACAGTCACC (SEQ ID No: 5), CTAACAGTCACA (SEQ ID No: 16), CTAGCAGTCACA (SEQ ID No: 17), CTAACAGTCACC (SEQ ID No: 18), CTAGCAGTCACC (SEQ ID No: 19), CTAACAGTCACC (SEQ ID No: 5), CTAGCAGTCACC (SEQ ID No: 20), CTAACAGTCACCC (SEQ ID No: 21) or CTAGCAGTCACCC (SEQ ID No: 22).

It will be appreciated that any number of nucleotides (e.g., up to 10, up to 20, up to 30 or up to 40 nucleotides) may be present at the 5' end of a primer that has a defined 3' end. A primer may have a 3' end that has at least 10, at least 15 or at least 20 nucleotides of complementarity with its target.

In another embodiment there is provided an isolated synthetic nucleic acid primer comprising a nucleic acid primer as listed in Table 1 (e.g. SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 11, SEQ ID No: 12, SEQ ID No: 16, SEQ ID No: 17, SEQ ID No: 18, SEQ ID No: 19, SEQ ID No: 20, SEQ ID No: 21 and SEQ ID No: 22).

In another example there is provided an isolated synthetic nucleic acid molecule having a 3' end of sequence according to SEQ ID No: 11 further comprising a restriction site, for example

```
                                              (SEQ ID No: 7)
CGCGCGGCCGCTCTCRCTCTAACAGTCACC,
``` wherein R is A or G.

In one embodiment there is provided a nucleic acid sequence that is capable of hybridizing to a site in SEQ ID No: 10.

In a further embodiment there is provided a PCR reagent comprising a pair of PCR primers, wherein the primer pair have a 3' end of sequence is selected from SEQ ID No: 11 and SEQ ID No: 1.

The PCR reagent may further comprise a forward and reverse heavy chain pair of primers having a 3' end of sequence selected from SEQ ID No: 3 and SEQ ID No: 4.

Reference to the term "PCR reagents" herein refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents contain a template from which a target sequence can be amplified.

In another embodiment the PCR reagent comprises a pair of PCR primers wherein the first primer is the light chain reverse primer having a 3' end of sequence according to SEQ ID No: 11 and the second primer is the light chain forward primer capable of hybridising to a site in SEQ ID No: 10. In one example the PCR reagent comprises a light chain reverse primer having a 3' end of sequence according to SEQ ID No: 11 and a light chain forward primer having a 3' end of sequence according to SEQ ID No: 1.

The PCR reagent may further comprise forward and reverse heavy chain pair of primers having a 3' end of sequence according to SEQ ID No: 3 and SEQ ID No: 4.

The PCR reagent may comprise forward and reverse primers which further comprise sequences that, in double stranded form, are cleavable by a restriction enzyme, for example having a 3' end of sequence according to SEQ ID No: 6, SEQ ID No: 7, SEQ ID No: 8 and SEQ ID No: 9.

The composition, in addition to the PCR reagents described above, further comprises a cDNA template derived from a hybridoma produced by fusing a B cell from an rabbit having a b4 allotype and a fusion partner having an allotype other than b4, for example a b5 allotype (e.g., a 240E cell or a derivative thereof). Specifically, cDNA according to SEQ ID No: 10 and/or SEQ ID No: 14.

According to a further aspect of the invention there is provided use of an isolated synthetic nucleic acid molecule having a 3' end of sequence according to SEQ ID No. 11, in the production of a recombinant antibody derived from a rabbit having a b4 allotype. In accordance with this aspect, the light chain reverse primer (SEQ ID No. 11) may be paired with any suitable light chain forward primer as described herein (e.g. SEQ ID No: 1, SEQ ID No: 6 or a primer capable of hybridising to a site in SEQ ID No:10) to produce a b4 kappa light chain. The forward and reverse heavy chain primers disclosed herein (SEQ ID No: 3 and SEQ ID No: 4) may be used in the production of a variable heavy chain domain which when expressed with heavy chain constant regions is capable of pairing with a b4 kappa light chain to produce a recombinant b4 antibody.

It will be appreciated that SEQ ID No: 3 and SEQ ID No: 4 represent non-limiting embodiments and it is within the remit of the person skilled in the art to use alternative primers that are capable of amplifying the full length coding sequence of a b4 variable heavy chain. Alternatively heavy chain primers which amplify the full length coding sequence of a b4 heavy chain may be used with the light chain primers described herein. Similarly, the b4 kappa light chain forward primer (SEQ ID No: 1) may be substituted with another primer capable of amplifying the kappa light chain when used in combination with a reverse kappa light chain primer defined according to the formula of SEQ ID No: 11.

Also provided herein is the use of an isolated synthetic nucleic acid molecule having a 3' end of sequence according to SEQ ID No: 2 in the production of a recombinant antibody derived from a rabbit having a b4 allotype. In an example, SEQ ID No: 2 may be paired with a light chain forward primer having a 3' end of sequence according to SEQ ID No: 1 or SEQ ID No: 6, and combined with a forward and reverse heavy chain primer having a 3' end of sequence according to SEQ ID No: 3 and SEQ ID No: 4 or SEQ ID No: 8 and SEQ ID No: 9 respectively to produce a recombinant b4 antibody.

Sequences

| Description | Sequence | SEQ ID No |
|---|---|---|
| 3' end of b4 kappa light chain forward primer | ATGGACACGAGGGCCCCCAC | 1 |
| 3' end of b4 kappa light chain reverse primer | CTAACAGTCX | 2 |
| 3' end of b4 heavy chain forward primer | ATGGAGACTGGGCTGCGCTGGCT | 3 |
| 3' end of b4 heavy chain reverse primer | CAGGCAGCCCAGGGTCAC | 4 |
| 3' end of b4 kappa light chain reverse primer | CTAACAGTCACC | 5 |
| 3' end of b4 kappa light chain forward primer. KpnI restriction site underlined. | CGCAAGCTTGTACCCTTCACCATGGACACGAGGGCCCCCAC | 6 |
| 3' end of b4 kappa light chain reverse primer. NotI restriction site underlined. | CGCGCGGCCGCTCTCRCTCTAACAGTCACC | 7 |
| 3' end of heavy chain forward primer. KpnI restriction site underlined. | CGGAAGCTTGTACCCTTCACCATGGAGACTGGCTGCGCTGGCT | 8 |
| 3' end of heavy chain reverse primer. HindIII restriction site underlined. | GGGAGGTACCCTTTGACCAGGCAGCCCAGGGTCAC | 9 |
| cDNA of 5' end of an exemplary kappa light chain | CAGTGCAGGCAGGACCCAGCATGGACACGAGGGCCCCCACTCAGCTGCTGGGGCTCCTGCTGCTCTGG | 10 |
| 3' end of b4 kappa light chain reverse primer | CTARCAGTCX | 11 |
| 3' end of b4 kappa light chain reverse primer | CTARCAGTCACC | 12 |
| Encoded amino acid sequence of SEQ ID No: 10 | MDTRAPTQLLGLLLLW | 13 |
| cDNA of 3' end of an exemplary kappa light chain | GGCACGACCTCAGTCGTCCAGAGCTTCAATAGGGGTGACTGTTAGAGCGAGACGCCTG | 14 |
| Encoded amino acid sequence of SEQ ID No: 14. | GTTSVVQSFNRGDC | 15 |
| 3' end of b4 kappa light chain reverse primer | CTAACAGTCACA | 16 |
| 3' end of b4 kappa light chain reverse primer | CTAGCAGTCACA | 17 |
| 3' end of b4 kappa light chain reverse primer | CTAACAGTCACC | 18 |

-continued

| Description | Sequence | SEQ ID No |
|---|---|---|
| 3' end of b4 kappa light chain reverse primer | CTAGCAGTCACC | 19 |
| 3' end of b4 kappa light chain reverse primer | CTAGCAGTCACC | 20 |
| 3' end of b4 kappa light chain reverse primer | CTAACAGTCACCC | 21 |
| 3' end of b4 kappa light chain reverse primer | CTAGCAGTCACCC | 22 |

The invention is described further in the following non-limiting examples.

Examples

The sequence motif distinguishing rabbit Kappa chain of allotype b4 to b5 was identified from a multiple alignment of all the known rabbit germline Kappa. Sequences were recovered from the IMGT database and sequences compared after multiple alignment using CLUSTALW. The primer was designed to incorporate at the 3'-end the four base-pairs that will distinguish b4 to b5 kappa chain allotype. As described below, the light chain primers described herein consistently amplify the kappa light chain with little off target amplification as shown by the absence of secondary bands in FIG. 3.

1. mRNA Extraction
   a. Add 1:1 v/v of lysis buffer (Qiagen Buffer TCL 2× w/ 2% 2-mercaptoethanol) to hybridoma cells
   b. Add 80 µl cell lysate to TurboCapture plate, incubate for 90 min on orbital shaker at 100 rpm
   c. Wash 3× w/ Buffer TCW (leave last wash until adding RT PCR mix)
   d. Proceed to cDNA synthesis immediately (don't use Tris-HCL buffer due to possible inhibition of cDNA synthesis or mRNA degradation)
2. cDNA Synthesis
   a. Remove residual Buffer TCW
   b. Add 80 ul RT mix

| Component | Volume (µl) |
|---|---|
| Nuclease free dH₂O | 46.4 |
| 5× Reaction buffer (supplied with RT) | 16 |
| 25 mM MgCl₂ (supplied with RT; final concentration 3 mM) | 9.6 |
| 10 mM dNTP mixture (final concentration 0.5 mM) | 4 |
| RNaseOUT Ribonuclease Inhibitor (160 Units/80 µl reaction) | 2 |
| ImProm-II Reverse Transcriptase (RT) | 2 |
| Total reaction volume/well | 80 | c. Start reaction "RT1" on thermal cycler

| 25° C. | 5 min |
|---|---|
| 40° C. | 60 min |
| 70° C. | 15 min |
| 4° C. | forever | d. Wash 3× w/ 10 mM Tris-HCL, leave last wash until PCR amplification of cDNA
3. PCR Amplification of H and L Chain Variable Regions
   a. Remove Tris-HCL
   b. Add 80 µl VH PCR mix (prepare mix on ice to avoid non-specific priming of active polymerase)

| Component | Volume (µl) |
|---|---|
| Nuclease free dH₂O | 52.9 |
| 10X TaqPlus Precision buffer | 8 |
| 10 mM dNTP mixture (final concentration 0.2 mM) | 1.6 |
| 3 µM light chain reverse primer | 4 |
| 3 µM light chain forward primer | 4 |
| 3 µM heavy chain forward primer | 4 |
| 3 µM heavy chain reverse primer | 4 |
| TaqPlus Precision Polymerase | 1.5 |
| Total reaction volume/well | 80 |

RabMab (Rabbit Monoclonal Antibody) Primers

```
Heavy Chain:
VH Forward (OYZ64-2)
                                       (SEQ ID NO: 8)
5'-CGGAAGCTTGTACCCTTCACCATGGAGACTGGGCTG
CGCTGGCT-3'

VH Reverse (OYZvh3)
                                       (SEQ ID NO: 9)
5'-GGGAGGTACCCTTTGACCAGGCAGCCCAGGGTCAC-3'

Light Chain (Full length):
Light chain forward (OYZ62)
                                       (SEQ ID NO: 6)
5'-CGCAAGCTTGTACCCTTCACCATGGACACGAGGGCCC
CCAC-3'

Light chain reverse (OYZ71)
                                       (SEQ ID NO: 7)
5'-CGCGCGGCCGCTCTCRCTCTAACAGTCACC-3'
``` a. Start reaction on thermal cycler

| 94° C. | 5 min | 1 cycle |
|---|---|---|
| 94° C. | 30 sec | 34 cycles |
| 58° C. | 30 sec | |
| 72° C. | 1 min | |
| 72° C. | 10 min | 1 cycle |
| 4° C. | forever | | b. Transfer and save PCR reaction mix to a new tube
   c. Resolve VH and Light chain bands on 1.2% agarose gel (40 ul, save the other 40 ul).

Purify VH and Light chain DNA from agarose gel (cut each band out, VH~650 bp and VL~850 bp) with QIAquick Gel Extraction Kit (final elution 50 ul)

4. Restriction Enzyme Digestion of PCR Products

Prepare the Digestion Mixture on Ice

| Component | Amount (μl) |
|---|---|
| Heavy chain PCR product | 45 |
| Hind III (add first and digest for 1 hr) | 1.5 |
| Kpn I (following 1 hr digestion with HindIII, add KpnI and digest for another 1 hr) | 1.5 |
| 10X NEB Buffer 2 | 10 |
| 10X BSA | 10 |
| dH$_2$O | 32 |
| Total Reaction Volume | 100 |

| Component | Amount (μl) |
|---|---|
| Light chain PCR product | 45 |
| Hind III | 1.5 |
| Not I | 1.5 |
| 10X NEB Buffer 2 | 10 |
| 10X BSA | 10 |
| dH2O | 32 |
| Total Reaction Volume | 100 | a. Incubate for 2 hr in a 37° C. water bath (for the heavy chain, digest with HindIII first for 1 hr then add KpnI for another 1 hr)
b. Purify digested products by QIAquick PCR purification kit (no need for gel purification)

5. Restriction Enzyme Digestion of Plasmids

Prepare the Digestion Mixture on Ice

| Component | Amount (μl) |
|---|---|
| Heavy chain plasmid (5 ug) | (5 ug) |
| Hind III | 3 |
| Kpn I (can add together with HindIII for plasmid digestions) | 3 |
| 10X NEB Buffer 2 | 10 |
| 10X BSA | 10 |
| dH$_2$O | Remaining up to 100 ul |
| Total Reaction Volume | 100 |

| Component | Amount (μl) |
|---|---|
| Light chain plasmid (5 ug) | (5 ug) |
| Hind III | 3 |
| Not I | 3 |
| 10X NEB Buffer 2 | 10 |
| 10X BSA | 10 |
| dH$_2$O | Remaining up to 100 ul |
| dH2O | Remaining up to 100 ul |
| Total Reaction Volume | 100 | a. Incubate for 2 hr in a 37° C. water bath
b. Heat inactivate enzymes at 65° C. water bath for 20 mins
c. Treat vectors with CIP to prevent self-ligation: add 1 ul CIP+11 ul 10×NEB Buffer 3 to 100 ul of above reaction (instead of CIP you can use 1 ul Antarctic Phosphatase+11 ul Antarctic Phosphatase Buffer to 100 ul reaction)
d. Incubate for 1 hr at 37° C. (if using Antarctic Phosphatase, heat inactivate for 5 mins at 65° C.)
e. Purify by agarose gel purification (vector ~4.6 kb, remove variable region insert) with QIAquick Gel Extraction Kit (final elution volume 50 ul)

6. Ligation of VH and Light Chain Inserts into Vector a. Run inserts and vector (3 ul) on the same 1.2% agarose gel
b. Based on the band intensity, estimate the amount of DNA to use. Approximate 1:3 and 1:5 vector to insert molar ratio.
c. Based on a total ligation reaction volume of 10 ul (components=vector+insert+0.5 ul T4 DNA ligase+1 ul 10×T4 DNA ligase buffer+up to 10 ul dH$_2$O), add the appropriate amount of vector+insert+water (up to 8.5 ul dH$_2$O) in a small PCR reaction tube, leaving out ligase and buffer.
d. Heat tube containing vector+insert+water in a 42° C. water bath for 3 mins with the cap open to evaporate remaining alcohol from gel extraction procedure (do not include ligase and buffer).
e. Add 0.5 ul T4 DNA ligase+1 ul 10× buffer
f. Incubate one hour at RT

| Component | Amount (μl) |
|---|---|
| Heavy chain insert (HindIII/KpnI) | |
| vector (HindIII/KpnI/CIP) | |
| T4 DNA ligase | 0.5 |
| 10X T4 DNA ligase buffer | 1 |
| dH$_2$O | |
| Total Reaction Volume | 10 |

| Component | Amount (μl) |
|---|---|
| Light chain insert (digested with HindIII/NotI) | |
| vector (digested with HindIII/NotI) | |
| T4 DNA ligase | 0.5 |
| 10X T4 DNA ligase buffer | 1 |
| dH$_2$O | |
| Total Reaction Volume | 10 |

7. Transformation a. Add 1 ul ligation mix to 25 ul DH5a
b. 30 min on ice
c. 45 sec at 42° C.
d. 2 min on ice (immerse tube into ice)
e. Add 250 ul SOC
f. Incubate 1 hr at 37° C., 225 rpm
g. Spread 250 ul transformation mix to LB-Amp plates
h. Incubate at 37° C. for 16-20 hrs
i. Pick 5-10 colonies per clone and culture in 3 ml LB-Amp broth
j. Incubate at 37° C., 225 rpm, for 16-20 hrs
k. Use 1.5 ml culture ONLY to perform miniprep with QIAprep Spin Miniprep Kit
l. Digest 2 ul samples with appropriate enzymes (HindIII/KpnI for VH plasmid; HindIII/NotI for VL plasmid) for 1 hr at 37° C.; resolve DNA on agarose gel

| Component | Amount (μl) |
|---|---|
| Heavy chain plasmid | 2 |
| Hind III | 0.5 |
| Kpn I | 0.5 |
| 10X NEB Buffer 2 | 2 |
| 10X BSA | 2 |
| dH₂O | 13 |
| Total Reaction Volume | 20 |

| Component | Amount (μl) |
|---|---|
| Light chain plasmid | 2 |
| Hind III | 0.5 |
| Not I | 0.5 |
| 10X NEB Buffer 2 | 2 |
| 10X BSA | 2 |
| dH₂O | 13 |
| Total Reaction Volume | 20 | m. Pick up the correct clones samples, take 5 ul DNA to 95 ul H₂O (1:20 dilution) to measure OD260 nm to determinate the DNA concentration. Dilute the samples to 100 ng/ul, take 5 ul for sequencing Results Splenocytes from several b4 rabbits were fused with a derivative of 240E using the method described in U.S. Pat. No. 7,429,487. Full length light chain amplicons were amplified from cDNA made from all of the hybridomas that were tested (FIG. 3) using the method described above, i.e., using a forward primer of sequence CGCAAGCTTGTACCCTT CACCATGGACACGAGGGCCCCCAC (SEQ ID NO: 6) and a reverse primer of sequence CGCGCGGCCGCTCTCRCTCTAACAGTCACC (SEQ ID NO: 7). FIG. 3 shows that the light chain primers described herein can be used to reproducibly amplify the kappa light chain with little off target amplification (secondary bands). No products were obtained from the 240E control (not shown). Selected amplicons were cloned into an expression vector, recombinant vectors were introduced into HEK-293 cells and the encoded light chain was expressed along with a corresponding full length heavy chain. Recombinant antibodies were produced and harvested from culture medium.

REFERENCES

1. Bystryn, J. C. et al, 1982, "Comparison of cell surface human melanoma-associated antigens identified by rabbit and murine antibodies", Hybridoma, 1: 465-72.
2. Weller, A. et al, 1987 "Preparation and properties of monoclonal and polyclonal antibodies to mouse epidermal growth factor (EGF) receptors: Evidence for cryptic EGF receptors in embryonal carcinoma cells.", Development, 100: 351-63.
3. Raybould, T. J, & Takahashi, M., 1988, "Production of stable rabbit-mouse hybridomas that secrete rabbit mAb of defined specificity" Science, 240: 1788-90.
4. Helga Spieker-Polet et al, 1995, "Rabbit monoclonal antibodies: Generating a fusion partner to produce rabbit-rabbit antibodies", Proc. Natl. Acad. Sci. USA, 92: 9348-9352.
5. Weimin Zhu, Guo-Liang Yu, "Rabbit Hybridoma" Book Chapter p 151-168. "Therapeutic Monoclonal Antibodies: from bench to clinic", A John Wiley & Sons, Inc., Publication 2009.
6. Weimin Zhu, "Rabbit Monoclonal Antibody: a New Diagnostics Technology", p 22-28, IVD TECHNOLOGY, SPRING 2013.

The invention claimed is:

1. A method for producing a recombinant antibody having a b4 allotype, the method comprising the steps of:
   a) providing a rabbit antibody-producing B-lymphocyte having a b4 allotype;
   b) fusing the B-lymphocyte of step a) with a rabbit fusion partner having a b5 allotype to produce a hybridoma cell capable of producing an antibody;
   c) making total cDNA from the hybridoma;
   d) amplifying the heavy chain and the b4 light chain from the cDNA of step c) using:
      (i) a light chain primer pair that comprises a forward primer having at the 3' end the nucleotide sequence of SEQ ID NO: 1 and a reverse primer of 15-60 nucleotides in length having at the 3' end the nucleotide sequence of SEQ ID NO: 12, 21 or 22, wherein the 3' terminal nucleotide of the reverse primer is the 3' terminal nucleotide of SEQ ID NO: 12, 21 or 22, and
      (ii) a heavy chain primer pair that amplifies the coding sequence for the variable domain of the heavy chain;
   e) cloning the amplified heavy chain and the light chain obtained in step d) into one or more plasmids downstream of an expression control sequence;
   f) transfecting the plasmids into a mammalian host cell capable of expressing an antibody;
   g) culturing the mammalian host cells under conditions suitable for antibody production;
   h) isolating the antibodies produced in step g);
   i) purifying the antibodies obtained in step h).

2. The method according to claim 1, wherein the light chain reverse primer has the 3' end of sequence CTARCAGTCACC (SEQ ID NO: 12), wherein the 3' terminal nucleotide of the reverse primer is the 3' terminal nucleotide of SEQ ID NO: 12.

3. The method of claim 1, wherein the one or more plasmids comprises a promoter and terminator for expression of the light chain of a monoclonal antibody in a cell.

4. The method of claim 1, wherein the light chain primer pair and the heavy chain primer pair of (d) (i) and (d) (ii), respectively, further comprise sequences that, in double stranded form, are cleavable by a restriction enzyme.

5. The method of claim 1, wherein said fusion partner is 240E1-1-2, as deposited at the ATCC as accession number HB-11870.

6. The method according to claim 1 wherein the heavy chain primer pair comprises a forward primer having at the 3' end the nucleotide sequence of SEQ ID No: 3 and a reverse primer having at the 3' end the nucleotide sequence of SEQ ID No: 4.

7. The method according to claim 1 wherein the rabbit fusion partner having a b5 allotype is selected from 240E, 240E-1, 240E-1-1-2, 240E-W and 240E-W2.

8. A composition comprising:
   a) cDNA from a rabbit hybridoma, wherein the cDNA comprises:
      i. cDNA molecules encoding the variable domain of a rabbit immunoglobulin light chain that has a b4 allotype,
      ii. cDNA molecules encoding the variable domain of a rabbit immunoglobulin light chain that has a b5 allotype;
      iii. cDNA molecules encoding the variable domain of a rabbit immunoglobulin heavy chain; and
   b) a PCR reagent comprising (i) a light chain primer pair that comprises a forward primer having at the 3' end the nucleotide sequence of SEQ ID NO: 1 and a reverse primer of 15-60 nucleotides in length having at the 3' end the nucleotide sequence of SEQ ID NO: 12, 21 or 22, wherein the 3' terminal nucleotide of the reverse primer is the 3' terminal nucleotide of SEQ ID NO: 12, 21 or 22; and (ii) a heavy chain primer pair that amplifies the coding sequence for the immunoglobulin heavy chain variable domain.

9. The composition of claim 8, wherein the reverse primer of (b) (i) has the 3' end of sequence CTARCAGTCACC (SEQ ID NO:12), wherein the 3' terminal nucleotide of the reverse primer is the 3' terminal nucleotide of SEQ ID NO: 12.

10. The composition of claim 8, wherein the light chain primer pair and the heavy chain primer pair comprise sequences that, in double stranded form, are cleavable by a restriction enzyme.

11. The composition according to claim 8 wherein the heavy chain primer pair comprises a forward primer having at the 3' end the nucleotide sequence of SEQ ID No: 3 and a reverse primer having at the 3' end the nucleotide sequence of SEQ ID No: 4.

* * * * *

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_Feature
<222> LOCATION: (1)..(20)
<223> OTHER INFORMATION: 3 end of b4 kappa light chain forward primer

<400> SEQUENCE: 1
atggacacga gggcccccac                                                    20

<210> SEQ ID NO 2
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_Feature
<222> LOCATION: (1)..(10)
<223> OTHER INFORMATION: 3 end of b4 kappa light chain reverse primer

<400> SEQUENCE: 2
ctaacagtca                                                               10
```

<210> SEQ ID NO 3
<211> LENGTH: 23
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(23)
<223> OTHER INFORMATION: 3 end of b4 heavy chain forward primer

<400> SEQUENCE: 3
atggagactg ggctgcgctg gct                                              23

<210> SEQ ID NO 4
<211> LENGTH: 18
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_Feature
<222> LOCATION: (1)..(18)
<223> OTHER INFORMATION: 3 end of b4 heavy chain reverse primer

<400> SEQUENCE: 4
caggcagccc agggtcac                                                    18

<210> SEQ ID NO 5
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(12)
<223> OTHER INFORMATION: 3 end of b4 kappa light chain reverse primer

<400> SEQUENCE: 5
ctaacagtca cc                                                          12

<210> SEQ ID NO 6
<211> LENGTH: 41
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(41)
<223> OTHER INFORMATION: 3 end of b4 kappa light chain forward primer

<400> SEQUENCE: 6
cgcaagcttg tacccttcac catggacacg agggccccca c                          41

<210> SEQ ID NO 7
<211> LENGTH: 30
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(30)
<223> OTHER INFORMATION: 3 end of b4 kappa light chain reverse primer
<220> FEATURE:
<221> NAME/KEY: Misc_feature
<222> LOCATION: (16)..(16)
<223> OTHER INFORMATION: n is "g" or "a"

<400> SEQUENCE: 7
cgcgcggccg ctctcnctct aacagtcacc                                    30

<210> SEQ ID NO 8
<211> LENGTH: 44
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(44)
<223> OTHER INFORMATION: 3 end of heavy chain forward primer

<400> SEQUENCE: 8
cggaagcttg taccctccac catggagact gggctgcgct ggct                    44

<210> SEQ ID NO 9
<211> LENGTH: 35
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(35)
<223> OTHER INFORMATION: 3 end of heavy chain reverse primer

<400> SEQUENCE: 9
gggaggtacc ctttgaccag gcagcccagg gtcac                              35

<210> SEQ ID NO 10
<211> LENGTH: 68
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(68)
<223> OTHER INFORMATION: cDNA of 5 end of an exemplary kappa light chain

<400> SEQUENCE: 10
cagtgcaggc aggacccagc atggacacga gggcccccac tcagctgctg gggctcctgc   60
tgctctgg                                                            68

<210> SEQ ID NO 11
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(10)
<223> OTHER INFORMATION: 3 end of b4 kappa light chain reverse primer
<220> FEATURE:
<221> NAME/KEY: Misc_feature
<222> LOCATION: (4)..(4)
<223> OTHER INFORMATION: n is "g" or "a"
<220> FEATURE:
<221> NAME/KEY: Misc_feature
<222> LOCATION: (11)..(13)
<223> OTHER INFORMATION: n is c or absent

<400> SEQUENCE: 11
ctancagtca nnn                                                      13

```
<210> SEQ ID NO 12
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(12)
<223> OTHER INFORMATION: 3 end of b4 kappa light chain reverse primer
<220> FEATURE:
<221> NAME/KEY: Misc_feature
<222> LOCATION: (4)..(4)
<223> OTHER INFORMATION: n is "g" or "a"

<400> SEQUENCE: 12
ctancagtca cc                                                           12

<210> SEQ ID NO 13
<211> LENGTH: 16
<212> TYPE: PRT
<213> ORGANISM: Artificial Sequence
<220> FEATURE:
<223> OTHER INFORMATION: Synthetic sequence

<400> SEQUENCE: 13

Met Asp Thr Arg Ala Pro Thr Gln Leu Leu Gly Leu Leu Leu Leu Trp
1               5                   10                  15

<210> SEQ ID NO 14
<211> LENGTH: 58
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(58)
<223> OTHER INFORMATION: cDNA of 3 end of an exemplary kappa light chain

<400> SEQUENCE: 14
ggcacgacct cagtcgtcca gagcttcaat aggggtgact gttagagcga gacgcctg         58

<210> SEQ ID NO 15
<211> LENGTH: 14
<212> TYPE: PRT
<213> ORGANISM: Artificial Sequence
<220> FEATURE:
<223> OTHER INFORMATION: Synthetic sequence

<400> SEQUENCE: 15

Gly Thr Thr Ser Val Val Gln Ser Phe Asn Arg Gly Asp Cys
1               5                   10

<210> SEQ ID NO 16
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(12)
<223> OTHER INFORMATION: 3 end of b4 kappa light chain reverse primer

<400> SEQUENCE: 16
ctaacagtca ca                                                           12
```

```
<210> SEQ ID NO 17
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(12)
<223> OTHER INFORMATION: 3 end of b4 kappa light chain reverse primer

<400> SEQUENCE: 17
ctagcagtca ca                                                              12

<210> SEQ ID NO 18
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(12)
<223> OTHER INFORMATION: 3 end of b4 kappa light chain reverse primer

<400> SEQUENCE: 18
ctaacagtca cc                                                              12

<210> SEQ ID NO 19
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(12)
<223> OTHER INFORMATION: 3 end of b4 kappa light chain reverse primer

<400> SEQUENCE: 19
ctagcagtca cc                                                              12

<210> SEQ ID NO 20
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(12)
<223> OTHER INFORMATION: 3 end of b4 kappa light chain reverse primer

<400> SEQUENCE: 20
ctagcagtca cc                                                              12

<210> SEQ ID NO 21
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(13)
<223> OTHER INFORMATION: 3 end of b4 kappa light chain reverse primer

<400> SEQUENCE: 21
ctaacagtca ccc                                                             13
```

```
<210> SEQ ID NO 22
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(13)
<223> OTHER INFORMATION: 3 end of b4 kappa light chain reverse primer

<400> SEQUENCE: 22
ctagcagtca ccc                                                    13
```